US010559694B1

(12) United States Patent
Son et al.

(10) Patent No.: US 10,559,694 B1
(45) Date of Patent: *Feb. 11, 2020

(54) GRAPHENE TRANSISTORS ON MICROBIAL CELLULOSE

(71) Applicant: HRL Laboratories, LLC, Malibu, CA (US)

(72) Inventors: Kyung-Ah Son, Moorpark, CA (US); Baohua Yang, Temple City, CA (US); Hwa Chang Seo, Torrance, CA (US); Danny Wong, Montebello, CA (US); Jeong-Sun Moon, Moorpark, CA (US)

(73) Assignee: HRL Laboratories, LLC, Malibu, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/590,298

(22) Filed: May 9, 2017

Related U.S. Application Data

(62) Division of application No. 14/965,785, filed on Dec. 10, 2015, now Pat. No. 9,679,970.

(60) Provisional application No. 62/118,828, filed on Feb. 20, 2015, provisional application No. 62/118,424, filed on Feb. 19, 2015.

(51) Int. Cl.
*H01L 29/786* (2006.01)
*H01L 29/16* (2006.01)
*H01L 29/66* (2006.01)

(52) U.S. Cl.
CPC .... *H01L 29/78684* (2013.01); *H01L 29/1606* (2013.01); *H01L 29/66742* (2013.01)

(58) Field of Classification Search
None
See application file for complete search history.

(56) References Cited

U.S. PATENT DOCUMENTS

| 9,662,498 B1 * | 5/2017 | Son .................. A61N 1/36125 |
| 9,679,970 B1 | 6/2017 | Son et al. |
| 2010/0143681 A1 | 6/2010 | Yano et al. |
| 2011/0114971 A1 | 5/2011 | Sato |
| 2011/0147756 A1 | 6/2011 | Moriguchi et al. |
| 2012/0262449 A1 | 10/2012 | Jeon et al. |
| 2015/0144944 A1 | 5/2015 | Yang et al. |

OTHER PUBLICATIONS

Alcacer et al., "Biocellulose based materials for organic field effect transistors," Pro EUROCON and CONFTELE 2011, Lisbon, Portugal, 4 pages.

Alcacer et al., "Biocellulose based materials for organic field effect transistors," Pro EUROCON and CONFTELE 2011, Lisbon, Portugal, 4 pages, (Apr. 2011}.

Cohen-Karni et al., "Graphene and nanowire transistors for cellular interfaces and electrical recording," Nano Letters 10, pp. 1098-1102, (2010}.

(Continued)

*Primary Examiner* — Hoang-Quan T Ho
(74) *Attorney, Agent, or Firm* — Ladas & Parry (57) ABSTRACT

A device including a biopolymer membrane, a passivation layer on the biopolymer membrane, a graphene layer on the passivation layer, a source electrode on the graphene layer, and a drain electrode on the graphene layer, wherein the graphene layer extends between the source electrode and the drain electrode.

12 Claims, 12 Drawing Sheets

(56) References Cited

OTHER PUBLICATIONS

Hess et al., "Graphene transistors for bioelectronics," Proceedings of the IEEE, vol. 101, No. 7, pp. 1780-1792, (Jul. 2013}.
Pereira et al., "Bacterial cellulose as substrate for inkjet printing on organic thin film transistors," /COE 2012 Abstract.
Legnani et al. "Bacterial cellulose membrane as flexible substrate for organic light emitting devices." Science Direct I Elsevier. Jun. 10, 2008. Thin Solid Films. 517. pp. 1016-1020.
From U.S. Appl. No. 14/965,785 (now U.S. Pat. No. 9,679,970) Restriction Requirement dated May 25, 2016.
From U.S. Appl. No. 14/965,785 (now U.S. Pat. No. 9,679,970) Non Final Office Action dated Jul. 5, 2016.
From U.S. Appl. No. 14/965,785 (now U.S. Pat. No. 9,679,970) Final Office Action dated Nov. 7, 2016.
From U.S. Appl. No. 14/965,785 (now U.S. Pat. No. 9,679,970) Advisory Action dated Jan. 24, 2017.
From U.S. Appl. No. 14/965,785 (now U.S. Pat. No. 9,679,970) Notice of Allowance dated Feb. 15, 2017.

\* cited by examiner

GRAPHENE TRANSISTORS ON MICROBIAL CELLULOSE

CROSS REFERENCE TO RELATED APPLICATIONS

This application claims the benefit of and is a divisional of U.S. patent application Ser. No. 14/965,785 filed on Dec. 10, 2015, which relates to and claims the benefit of priority from U.S. Provisional Patent Application 62/118,424, filed Feb. 19, 2015 and U.S. Provisional Patent Application 62/118,828, filed Feb. 20, 2015.

STATEMENT REGARDING FEDERAL FUNDING

None

TECHNICAL FIELD

This disclosure relates to graphene transistors, and in vivo electronics and sensors.

BACKGROUND

In the prior art, various attempts have been made at realizing biocompatible and flexible sensors and electronics. Thin film transistors (TFTs) on various flexible substrates have been reported including organic TFTs, Si TFTs, carbon nanotube (CNT) and graphene FETs on polymer substrates, such as polyethylene terephthalate (PET), polyethylene naphthalate (PEN), and polyimide. However, the TFTs in the prior art have limited in vivo lifetime due to foreign body reactions in cells, such as fibrotic encapsulation or glial scarring, and also cause inflammation.

Graphene transistors having potential application for a cellular interface are described in "Graphene and nanowire transistors for cellular interfaces and electrical recording", Nano Letters 10, 1098 (2010). These graphene transistors are fabricated on an oxidized Si substrate with mechanically exfoliated graphene flakes using e-beam lithography. However, mechanically exfoliated graphene is not compatible with a micro-fabrication process, and it is not scalable. Further, the oxidized Si substrate described can damage tissues and nerves, which is a significant limitation against in vivo applications.

Solution-gated graphene transistors on an insulating rigid substrate are described in "Graphene transistors for bioelectronics", Proceed. of the IEEE 101, 1780 (2013). However, graphene transistors fabricated on a rigid surface are not well suited for in vivo use.

Transistors formed on a microbial cellulose substrate are described in "Biocellulose based materials for organic field effect transistors", Pro EUROCON and CONFTELE 2011, Lisbon, Portugal, and "Bacterial cellulose as substrate for inkjet printing on organic thin film transistors", ICOE 2012 Abstract. These two papers describe Pentacene- and RR-P3HT (regioregular poly(3-hexylthiophene)-based organic thin film transistors (OTFT) fabricated on a bacterial cellulose (i.e., microbial cellulose) film. Pentacene and RR-P3HT are organic semiconductors, which typically have very low carrier mobility (<5 $cm^2$/Vs). The FET mobility of the pentacene and RR-P3HT transistors on the bacterial cellulose are reported to be 0.0033 $cm^2$/Vs, and 0.057 $cm^2$/Vs, respectively. Due to the low carrier mobility, the pentacene and RR-P3HT transistors need to be operated with a high drain voltage (a few tens of volts) and a high gate potential (a few tens of volts). The slow speed and the high dissipation power are the major limitations to bioelectronics applications.

What is needed are biocompatible and flexible sensors and electronics that do not have these limitations. The embodiments of the present disclosure answer these and other needs.

SUMMARY

In a first embodiment disclosed herein, a device comprises a biopolymer membrane, a passivation layer on the biopolymer membrane, a graphene layer on the passivation layer, a source electrode on the graphene layer, and a drain electrode on the graphene layer, wherein the graphene layer extends between the source electrode and the drain electrode.

In another embodiment disclosed herein, a method of making a device comprises transferring a biopolymer membrane onto a handling wafer, forming a passivation layer on the biopolymer membrane, transferring graphene onto the passivation layer, patterning the graphene to form at least one graphene mesa, forming a source contact on a first edge of the graphene mesa, forming a drain contact on a second edge of the graphene mesa, etching the passivation layer surrounding the graphene mesa, the source contact, and the drain contact to expose the bio-polymer membrane, and releasing the bio-polymer membrane from the handling wafer.

These and other features and advantages will become further apparent from the detailed description and accompanying figures that follow. In the figures and description, numerals indicate the various features, like numerals referring to like features throughout both the drawings and the description.

DETAILED DESCRIPTION

In the following description, numerous specific details are set forth to clearly describe various specific embodiments disclosed herein. One skilled in the art, however, will understand that the presently claimed invention may be practiced without all of the specific details discussed below. In other instances, well known features have not been described so as not to obscure the invention.

The present disclosure describes biocompatible graphene transistors on a bio-integrative and bio-permeable membrane, microbial cellulose, for implantable ultra-flexible and conformal sensors and electronics with a long in vivo lifetime and describes related fabrication processes.

Figure 1A:
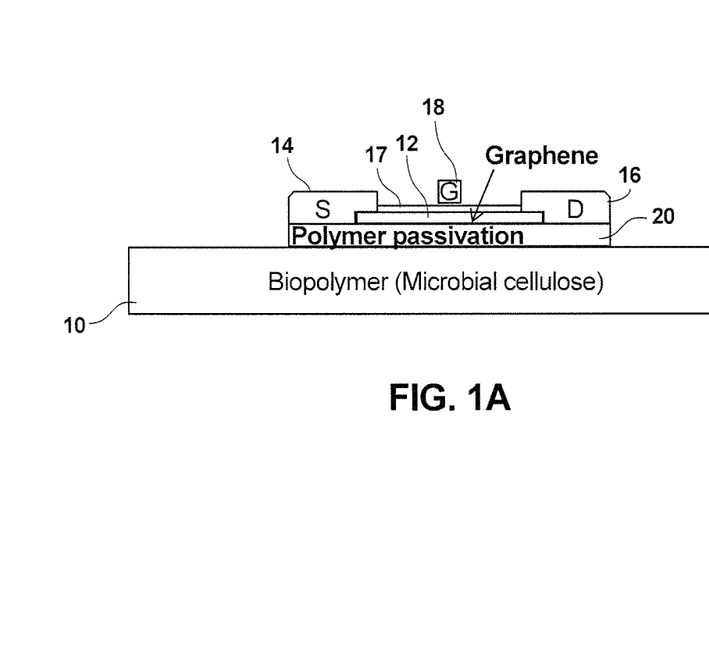
FIGS. 1A and 1B show a cross sectional schematic of a biocompatible graphene transistor fabricated on a bio-integrative biopolymer membrane, and a scanning electron microscope (SEM) image, respectively, in accordance with the present disclosure.

FIG. 1A shows a cross sectional schematic of a biocompatible graphene transistor fabricated on a bio-integrative biopolymer membrane 10. The channel 12 between the source 14 and the drain 16 may be graphene. A gate insulator 17, which may be a dielectric is on the graphene 12 and between the graphene 12 and a gate 18 to insulate the gate 18 from the graphene channel 12. The substrate 10 may be a biopolymer, such as microbial cellulose (MBC), and may be passivated with a polymer passivation layer 20, which may be SU-8, polyimide, parylene, or polydimethylsiloxane (PDMS). As further described in reference to FIGS. 3A, 3B and 3C, passivation of the substrate 10 may have alternate embodiments.

Figure 1B:
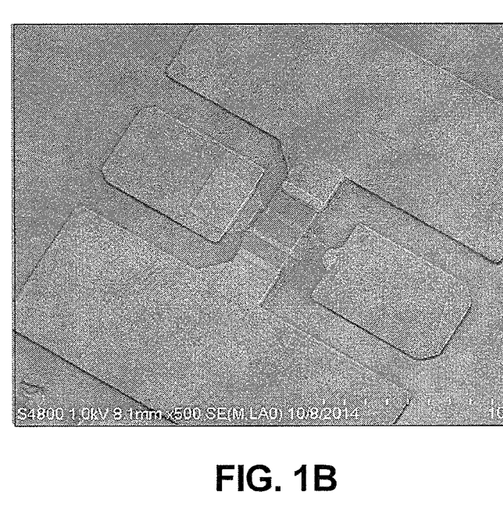

FIG. 1B shows a scanning electron microscope (SEM) image of a transistor fabricated on a biopolymer membrane 10 in accordance with the present disclosure.

The present disclosure describes the utilization of microbial cellulose as a substrate for biocompatible graphene transistors. Neurons can grow in such a substrate. Also described is a scalable microfabrication process for fabricating graphene transistors on a microbial cellulose membrane, which is fully compatible with conventional semiconductor device fabrication technologies. Use of a microbial cellulose membrane has a number of benefits including cell attachment and proliferation, no immunological reactions in the body, biocompatibility and chemical/mechanical stability in in vivo environments. Microbial cellulose has been previously used in the prior art as a tissue regeneration scaffold. In addition, microbial cellulose is commercially available at a low cost in a large scale in sheets and rolls, which is beneficial for developing large-scale fabrication processes compatible with roll-to-roll processes.

For in vivo medical diagnoses/monitoring, neural prosthetics, and brain-machine interfaces, significant research efforts have been expended to develop biocompatible and implantable sensors and electronics. In the prior art, biocompatibility of implantable sensors and electronics is largely attained by coating the sensors and electronics with biocompatible polymers, for example polyimide, polydimethylsiloxane (PDMS), and/or parylene. However, the delamination or cracking of polymer coatings results in limited in vivo lifetimes of the sensor probes and electronics. Further, the devices and probes fabricated with standard semiconductor micro fabrication technology are structurally rigid, and are invasive and incongruent to biological systems. Also, polymer-based flexible semiconductor devices in the prior art have a low carrier mobility (<80 cm$^2$/Vs), which results in reduced signal-to-noise ratio.

To address these limitations of the prior art implantable sensors and electronics, the present disclosure describes graphene FETs fabricated on a biocompatible and ultraflexible membrane for in vivo sensor and electronics applications. As described in the present disclosure, chemical vapor deposition (CVD)-grown graphene transferred onto an ultra-flexible biopolymer membrane provides high carrier mobility (>1,600 cm$^2$/Vs), high flexibility of up to 18% strain, and chemical stability suitable for in vivo conditions. The bio-membrane substrate can serve a scaffold for neuron/tissue regrowth, which is highly beneficial for realizing implantable devices with a long (>a few years) in vivo lifetime.

Figure 2:
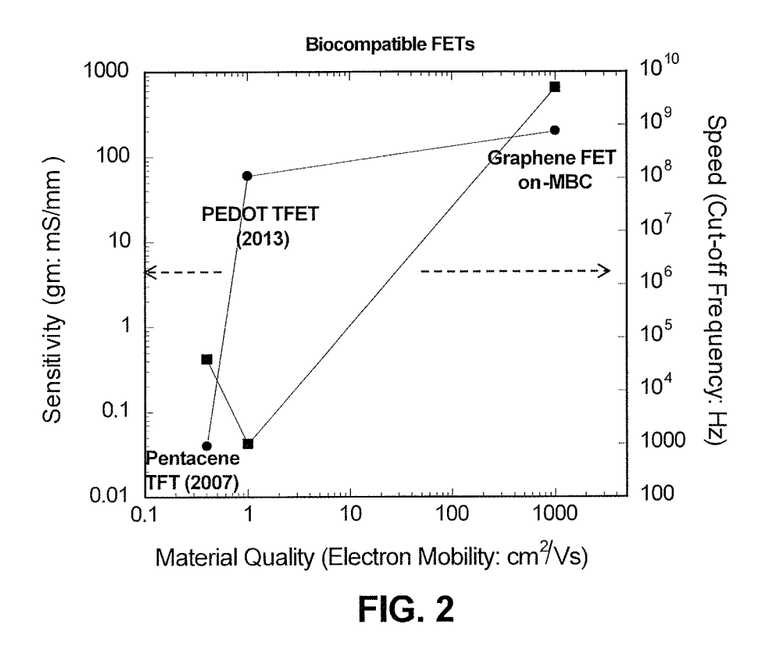
FIG. 2 shows a comparison of biocompatible and flexible transistors showing graphene FETs on a biopolymer membrane providing the highest carrier mobility, $g_m$ and cut-off frequency in accordance with the present disclosure.

FIG. 2 shows a comparison of prior art biocompatible and flexible transistors with the graphene FETs on a biopolymer membrane of the present disclosure. As shown in FIG. 2, graphene FETs on microbial cellulose (MBC) in accordance with the present disclosure have the highest sensitivity ($g_m$) and the highest cut-off frequency or speed compared to prior art pentacene TFTs and Poly(3,4-ethylenedioxythiophene) (PEDOT) TFTs.

Figure 3A:
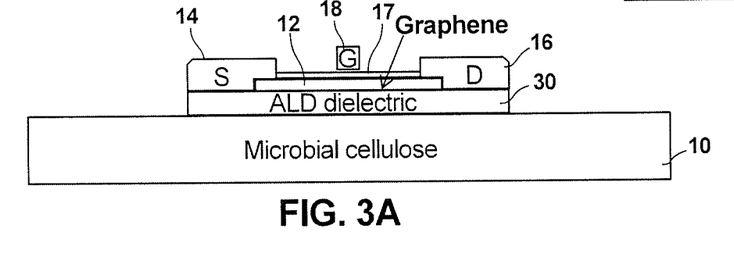
FIGS. 3A, 3B and 3C show cross sectional schematics of graphene FETs fabricated on microbial cellulose (MBC) in accordance with the present disclosure.
Figure 3B:
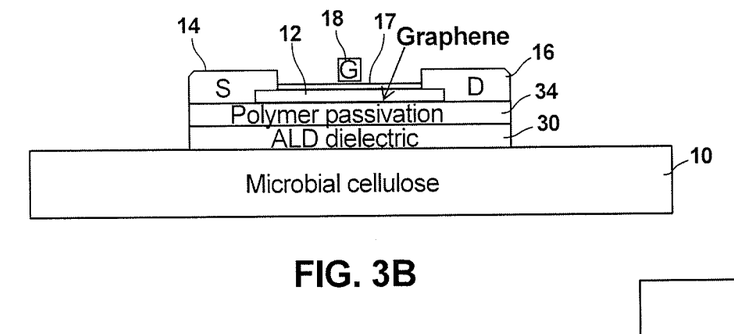
Figure 3C:
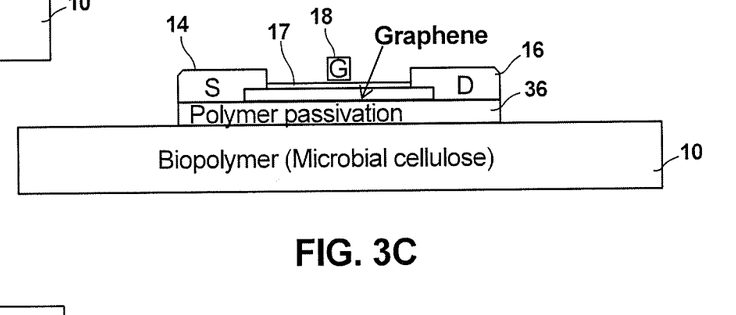

FIGS. 3A, 3B and 3C show cross sections of alternate embodiments of graphene FETs fabricated on microbial cellulose (MBC) in accordance with the present disclosure. As shown in FIG. 3A, the MBC 10 may be passivated with a dielectric film 30, such as Al$_2$O$_3$, SiO$_2$, or HfO$_2$ grown on the MBC 10 using atomic layer deposition (ALD). In an alternate embodiment, as shown in FIG. 3B, a dielectric such as Al$_2$O$_3$, SiO$_2$, or Hf 0$_2$ layer 30 may be grown on the MBC 10 using atomic layer deposition (ALD), and then a biocompatible polymer 34, such as SU-8, polyimide, parylene, or PDMS, is deposited on the dielectric. In yet another embodiment, as shown in FIG. 3C, a bio-compatible polymer 36, such as SU-8, polyimide, parylene, or PDMS, is used as a passivation layer on the MBC 10. In FIGS. 3A, 3B and 3C, for sensor applications, the gate dielectric 17 and gate electrode 18 are optional and may not be present, as for a sensor they may not be needed.

Figures 4A, 4B, 4C, 4D, 4E, 4F:
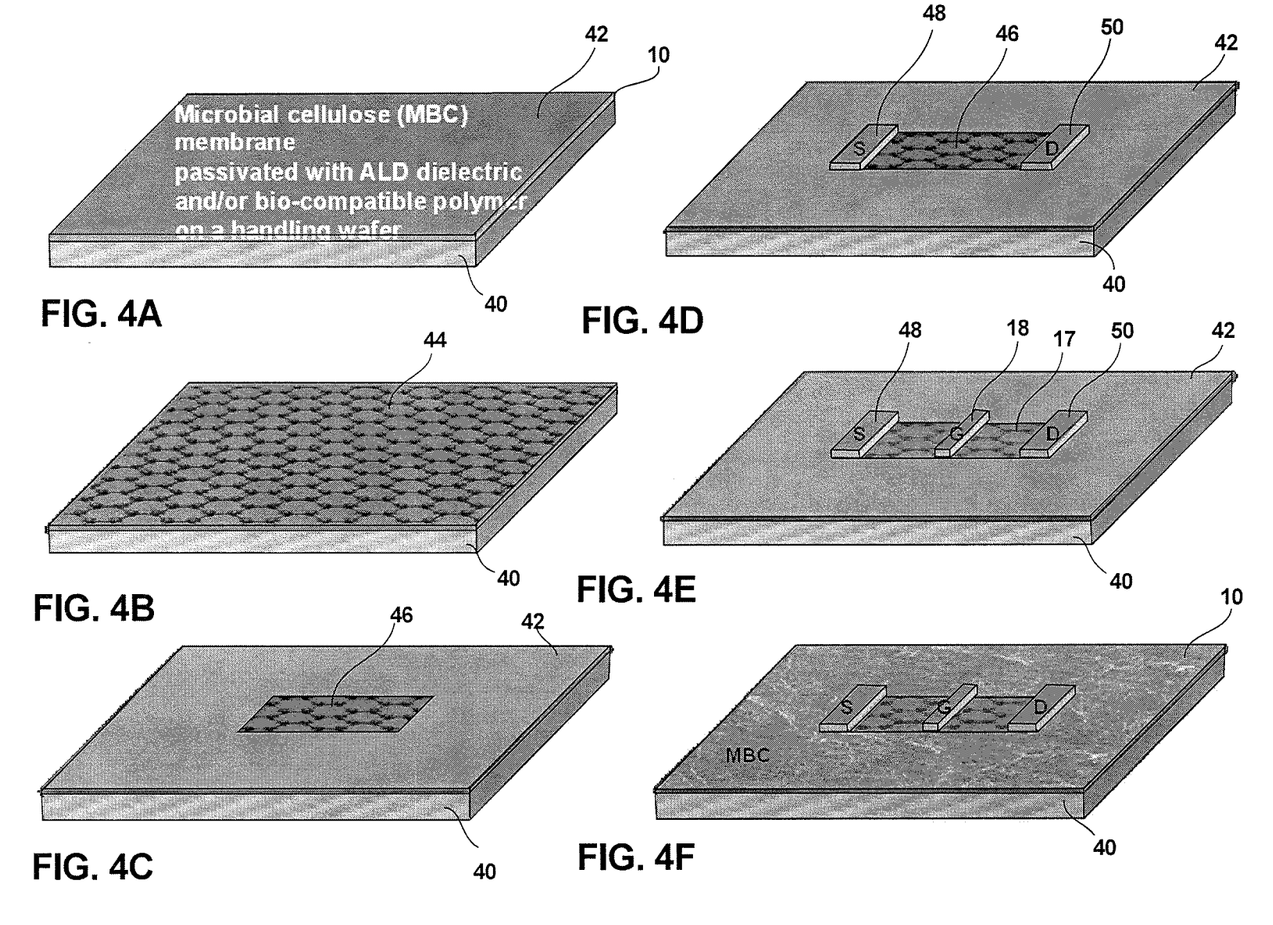
FIGS. 4A, 4B, 4C, 4D, 4E and 4F show a fabrication process for graphene field effect transistors (FETs) on a bio-polymer membrane, such as microbial cellulose (MBC), in accordance with the present disclosure.

FIGS. 4A, 4B, 4C, 4D, 4E and 4F show a fabrication process for graphene field effect transistors (FETs) on a bio-polymer membrane, such as microbial cellulose (MBC), in accordance with the present disclosure. As shown in FIG. 4A, a biopolymer 10, which may be a MBC membrane, is transferred on a handling wafer 40, which may be a common semiconductor or an insulator, such as Si, Ge, InP, GaAs, SiO$_2$, sapphire, quartz, or glass, and then dried in air. Then a passivation layer 42, which may be an ALD grown dielectric, such as an Al$_2$O$_3$, SiO$_2$, or HfO$_2$ layer, or a bio-compatible polymer such as SU-8, polyimide, parylene, or PDMS or a combination of both is applied over the MBC film 10. The thickness of the MBC membrane 10 may be less than 10 μm, the thickness of the passivation layer may be less than 10 nm for an ALD dielectric, and approximately 1 μm for a bio-compatible polymer. Next, as shown in FIG.

4B, a CVD graphene film 44 is transferred over the passivated MBC membrane. Next, as shown in FIG. 4C, the transferred graphene 44 may be patterned using a lithography methods well known in the art and etched with oxygen plasma to form graphene mesa structures 46, and to expose the passivation layer 42 surrounding the graphene mesa structures 46.

Then, as shown in FIG. 4D, an ohmic source 48 contact and an ohmic drain contact 50 are formed on edges of a graphene mesa 46. Next, as shown in FIG. 4E, a gate dielectric 17 is formed on the graphene mesa structure 46 and then a gate electrode 18 is formed on the gate dielectric 17 to complete a graphene FET. Then, as shown in FIG. 4F, the passivation layer 42 surrounding the graphene FET can be etched away from the background exposing the biopolymer membrane 10, which as described may be an MBC membrane. Finally the graphene FET and the MBC membrane may be released or demounted from the handling wafer 40.

FIGS. 5A, 5B, 5C, 5D, 5E and 5F show a fabrication process for a graphene-based bio-compatible sensor on a bio-polymer membrane, such as microbial cellulose (MBC), in accordance with the present disclosure. The process is similar to that described in reference to FIGS. 4A, 4B, 4C, 4D, 4E and 4F; however, for sensor applications, integration of a gate dielectric and a gate electrode is not needed.

Figures 5A, 5B, 5C, 5D, 5E, 5F:
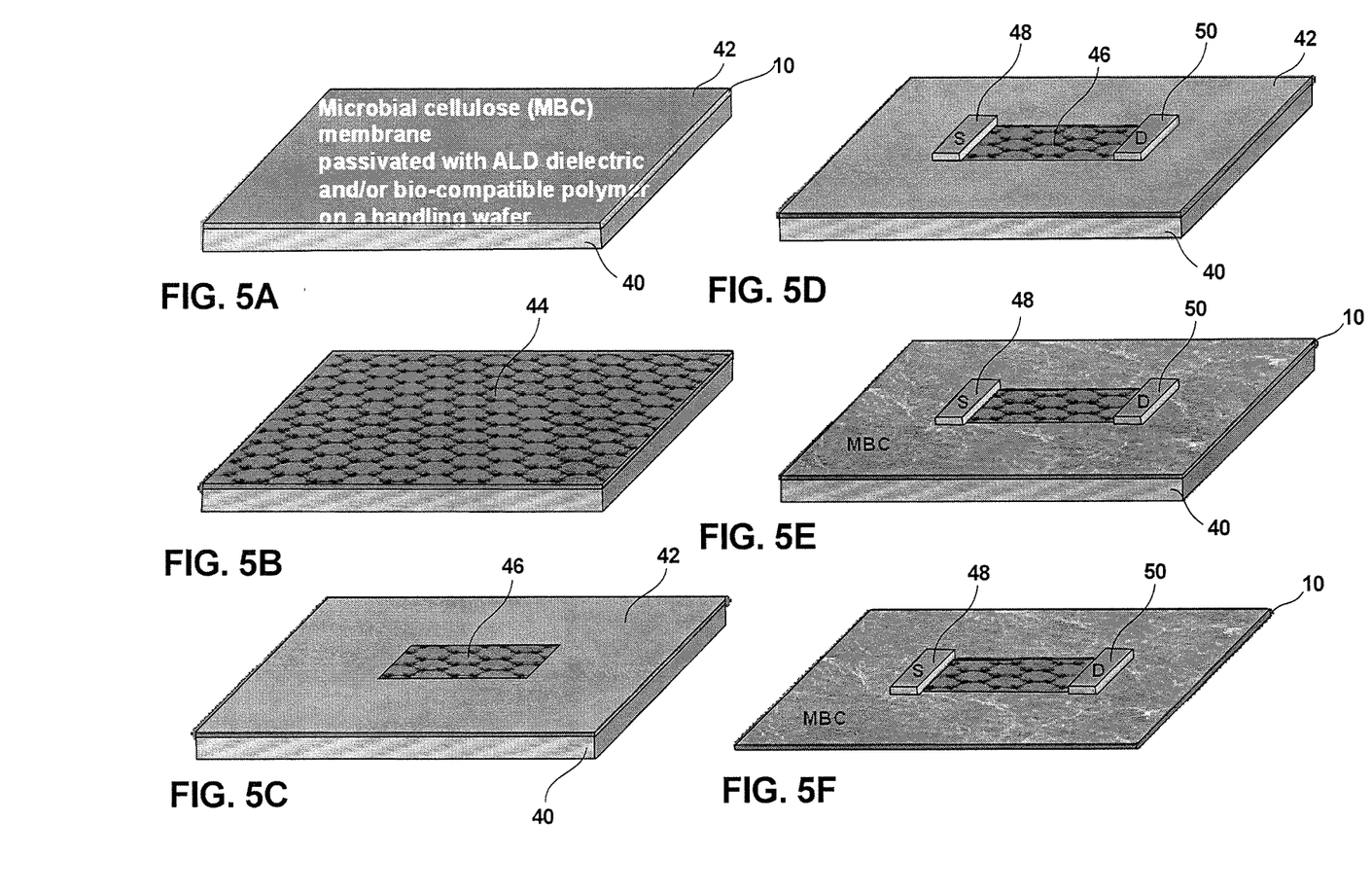
FIGS. 5A, 5B, 5C, 5D, 5E and 5F show a fabrication process for a graphene-based bio-compatible sensor on a bio-polymer membrane, such as microbial cellulose (MBC), in accordance with the present disclosure.

As shown in FIG. 5A, a MBC membrane 10 is transferred on a handling wafer 40, which may be a common semiconductor or an insulator, such as Si, Ge, InP, GaAs, $SiO_2$, sapphire, quartz, or glass, and then dried in air. Then a passivation layer 42, which may be an ALD grown dielectric, such as an $Al_2O_3$, $SiO_2$, or $HfO_2$ layer, or a biocompatible polymer such as SU-8, polyimide, parylene, or PDMS or a combination of both is applied over the MBC film 10. The thickness of each layer is usually less than 10 μm for the MBC membrane 10, less than 10 nm for an ALD dielectric, and approximately 1 μm for a bio-compatible polymer. Next, as shown in FIG. 5B, a CVD graphene film 44 is transferred over the passivated MBC membrane. Next, as shown in FIG. 5C, the transferred graphene 44 may be patterned using a lithography methods well known in the art and etched with oxygen plasma to form graphene mesa structures 46, and to expose the passivation layer 42 surrounding the graphene mesa structures 46.

Then, as shown in FIG. 5D, an ohmic source 48 contact and an ohmic drain contact 50 are formed on edges of a graphene mesa 46. Next, as shown in FIG. 5E, the passivation layer 42 surrounding the graphene-based bio-compatible sensor can be etched away from the background exposing the bio-polymer membrane 10, which as described may be an MBC membrane. Finally, as shown in FIG. 5F, the graphene-based bio-compatible sensor and the MBC membrane may be released or demounted from the handling wafer 40.

Figure 6A:
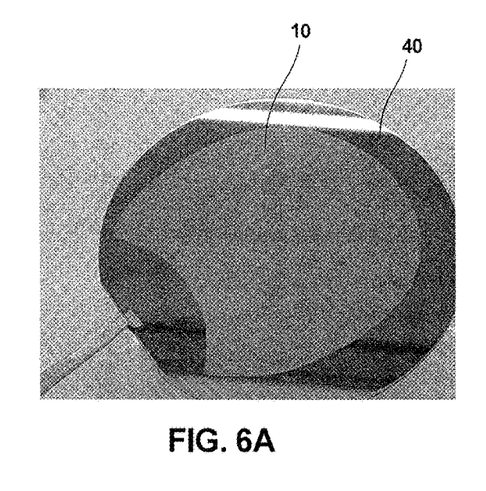
FIG. 6A shows a photograph of microbial cellulose (MBC) mounted on a Si handling wafer for processing.
Figure 6B:
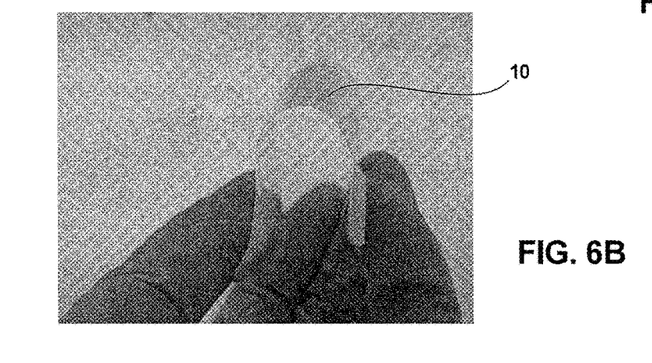
FIGS. 6B and 6C show an ultra-flexible MBC membrane passivated with SU-8 in accordance with the present disclosure.
Figure 6C:
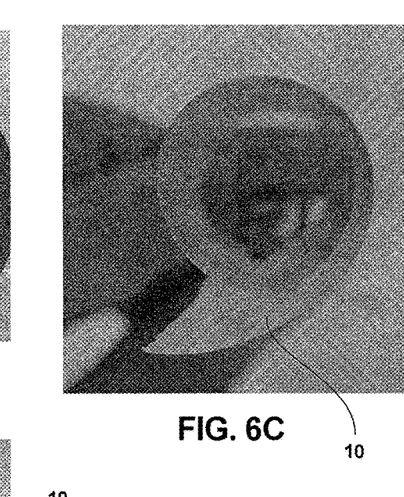

FIG. 6A shows a photograph of microbial cellulose (MBC) 10 mounted on a Si handling wafer 40 for processing, and FIGS. 6B and 6C show an ultra-flexible MBC membrane 10 passivated with a biocompatible polymer, namely SU-8.

Figure 7A:
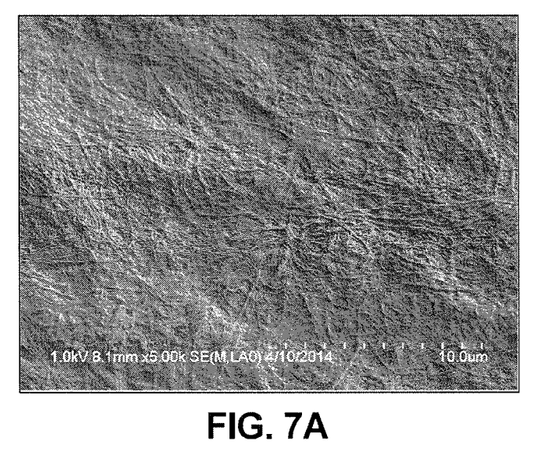
FIGS. 7A, 7B and 7C show SEM images of microbial cellulose (MBC) mounted on a handling wafer in accordance with the present disclosure.
Figure 7B:
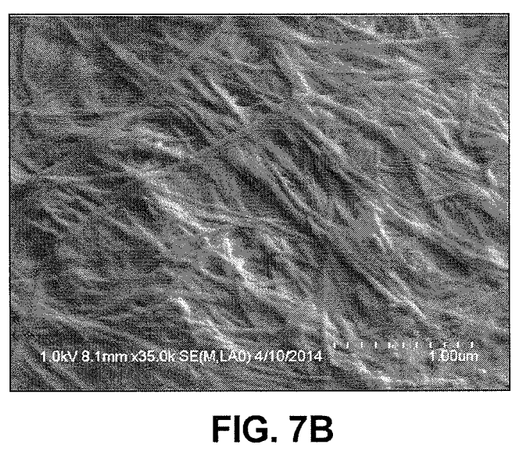
Figure 7C:
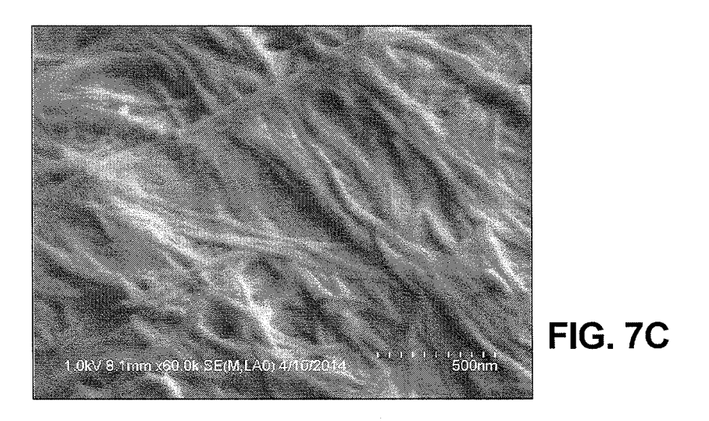

FIGS. 7A, 7B and 7C show SEM images of microbial cellulose (MBC) mounted on a Si handling wafer in accordance with the present disclosure. MBC consists of pure crystalline nano-fibrils, which have diameters of less than 50 nm and lengths of tens of μm.

Figure 8A:
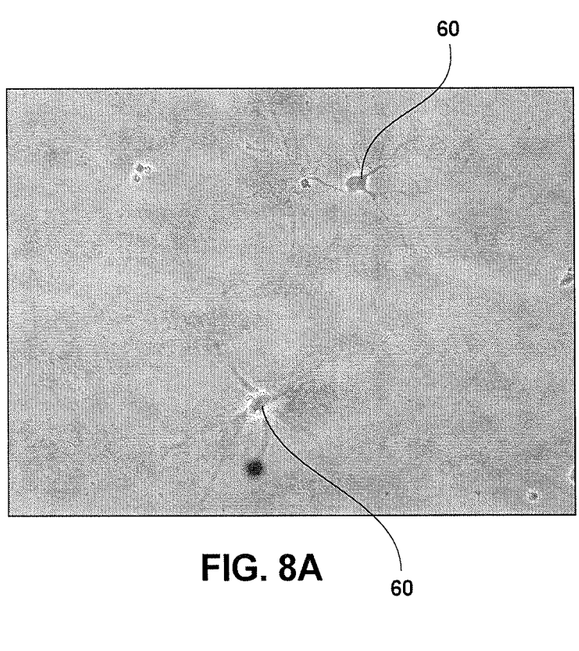
FIGS. 8A and 8B show optical microscope images of hippocampal neurons grown on MBC in accordance with the present disclosure.
Figure 8B:
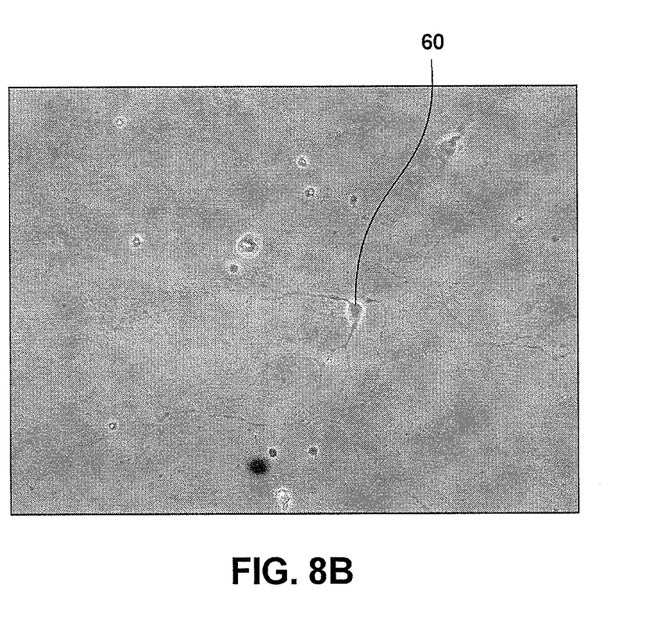

FIGS. 8A and 8B show optical microscope images of hippocampal neurons 60 grown on MBC. These images show that MBC is biocompatible and indicates the biointegrativity of MBC.

Figure 9A:
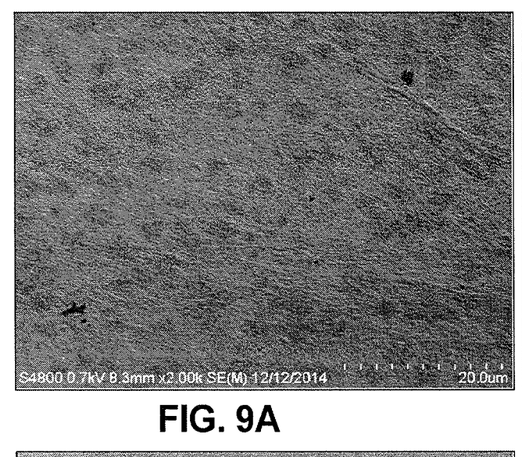
FIG. 9A and FIG. 9B, which is a detailed view of FIG. 9A, show SEM images of CVD graphene transferred on bare MBC and FIG. 9C and FIG. 9D, which is a detailed view of FIG. 9C, show MBC passivated with SU-8 in accordance with the present disclosure.
Figure 9B:
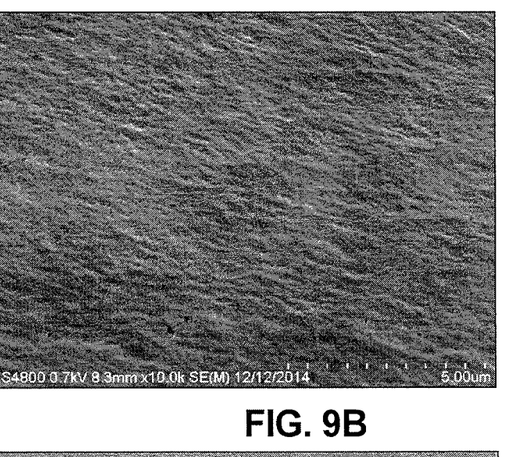
Figure 9C:
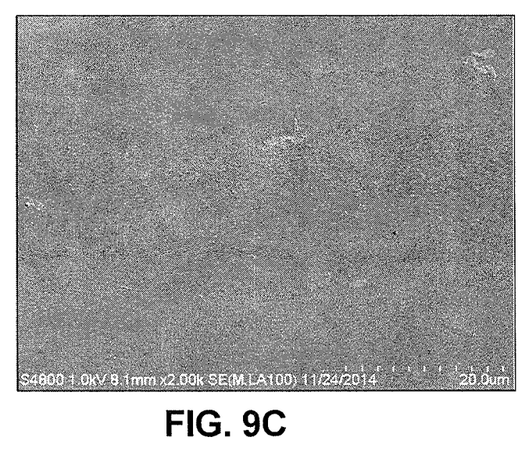
Figure 9D:
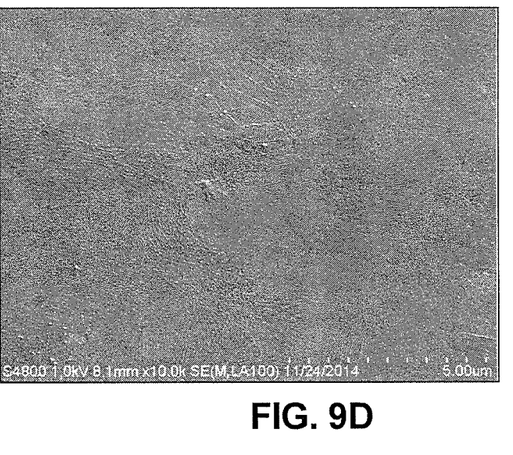

FIG. 9A and FIG. 9B, which is a detailed view of FIG. 9A, show SEM images of chemical vapor deposition (CVD)-grown graphene transferred on bare MBC. FIG. 9C and FIG. 9D, which is a detailed view of FIG. 9C, show MBC passivated with SU-8. The transferred graphene, shown in FIGS. 9A and 9B, is continuous across the entire sample and shows nearly no defects in the graphene caused by the transfer process. Minor defects in the images originate from growth defects in the CVD graphene. The sheet resistance and carrier mobility of the transferred graphene has been measured to be in the range of 450-1100 ohm/sq and 1600-2050 $cm^2$/Vs, respectively.

Figure 10:
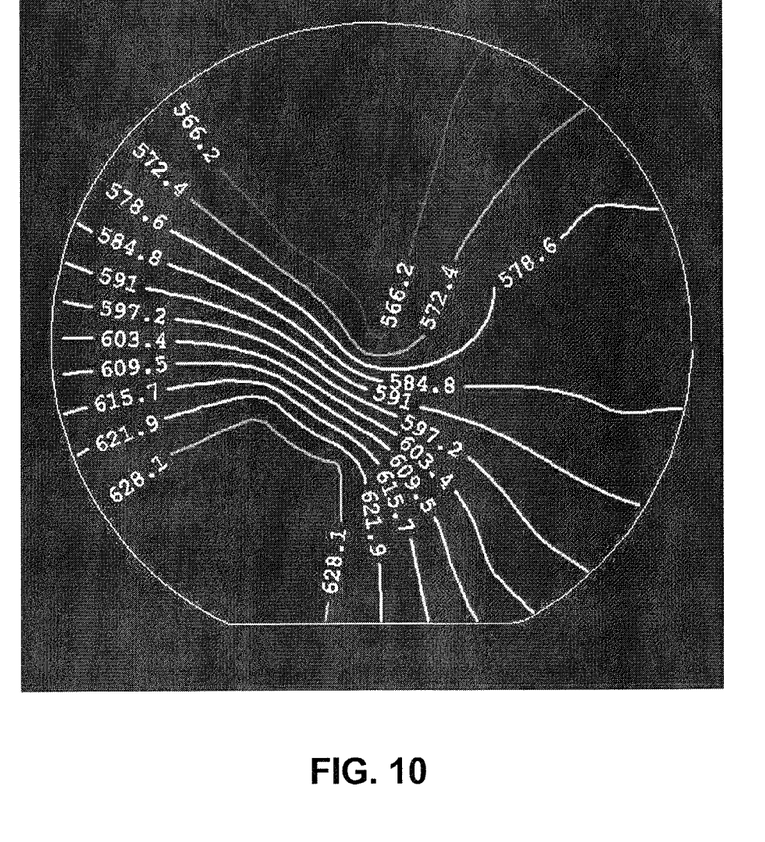
FIG. 10 shows a sheet resistance map of CVD graphene transferred on MBC passivated with SU-8 in accordance with the present disclosure.

FIG. 10 shows a sheet resistance map of CVD graphene transferred on MBC passivated with SU-8. The average sheet resistance $R_s$ is approximately 590 Ω/sq.

Figure 11:
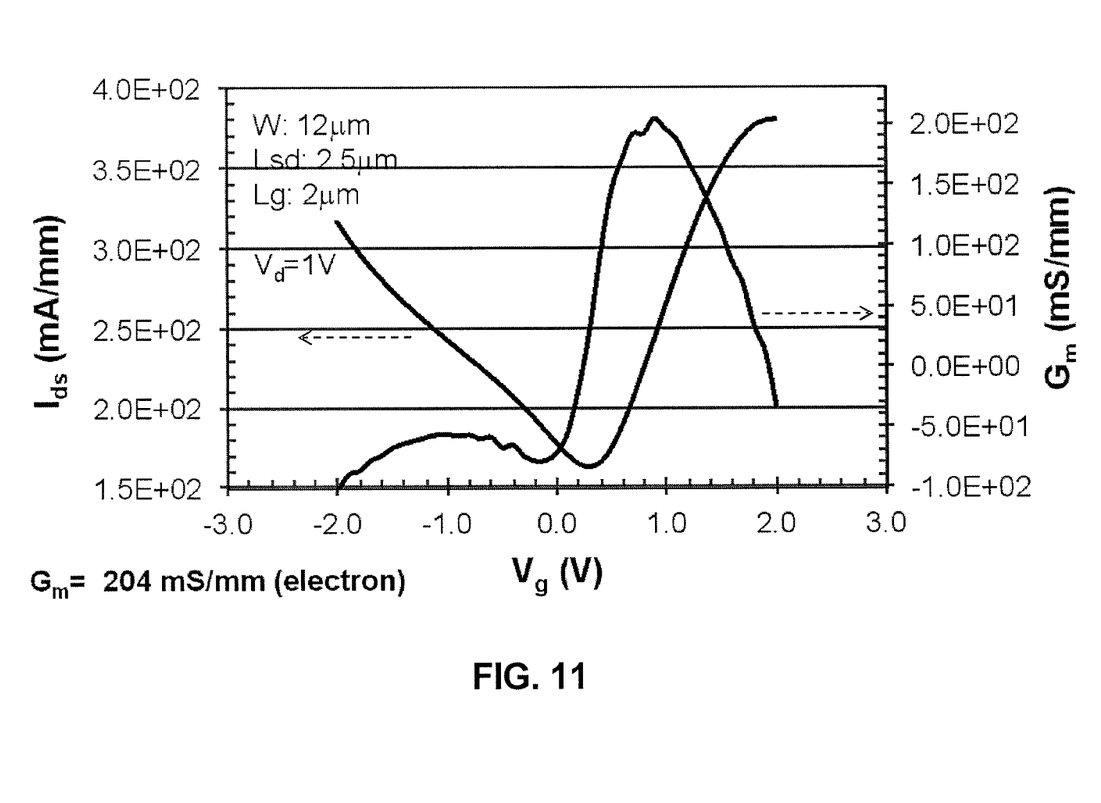
FIG. 11 shows transfer ($I_{ds}$) and transconductance ($G_m$) curves of a graphene FET fabricated on MBC in accordance with the present disclosure.

FIG. 11 shows the transfer ($I_{ds}$) and transconductance ($G_m$) curves, respectively, for a graphene FET fabricated on MBC. The contact resistance of ohmic contacts measured using transmission line measurement (TLM) patterns is less than 0.1 Ωmm, which is one of the lowest contact resistance values that has been reported in the prior art for graphene FETs. A high $G_m$ of 204 mS/mm is measured at $V_{ds}$=1V for a graphene FET with $L_g$=2 μm, $L_{sd}$=2.5 μm, W=12 μm. The high $G_m$ enables high sensitivity for sensing.

Figure 12A:
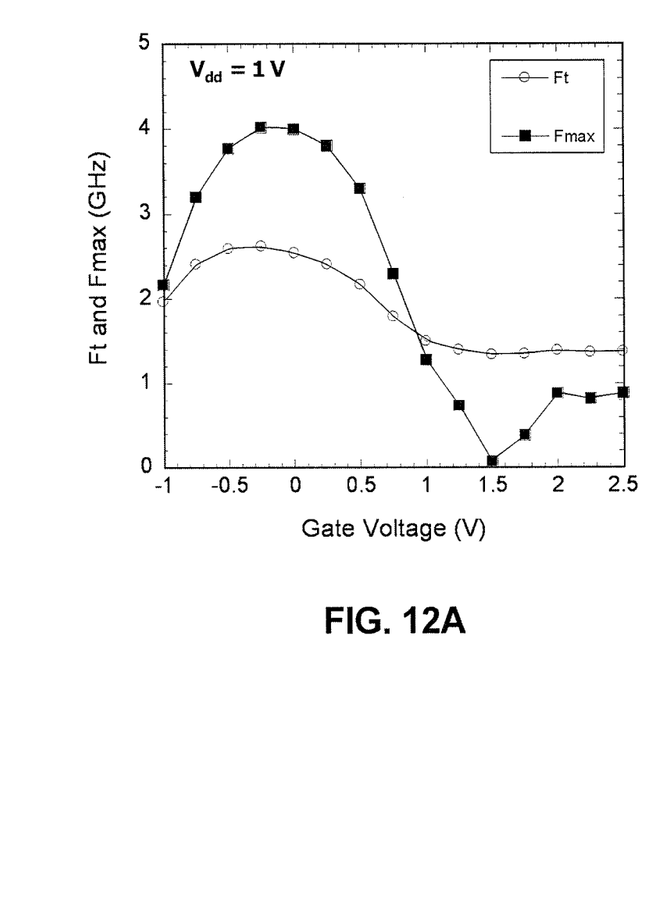
FIGS. 12A and 12B show radio frequency (RF) characteristics of a graphene FET fabricated on MBC in accordance with the present disclosure.
Figure 12B:
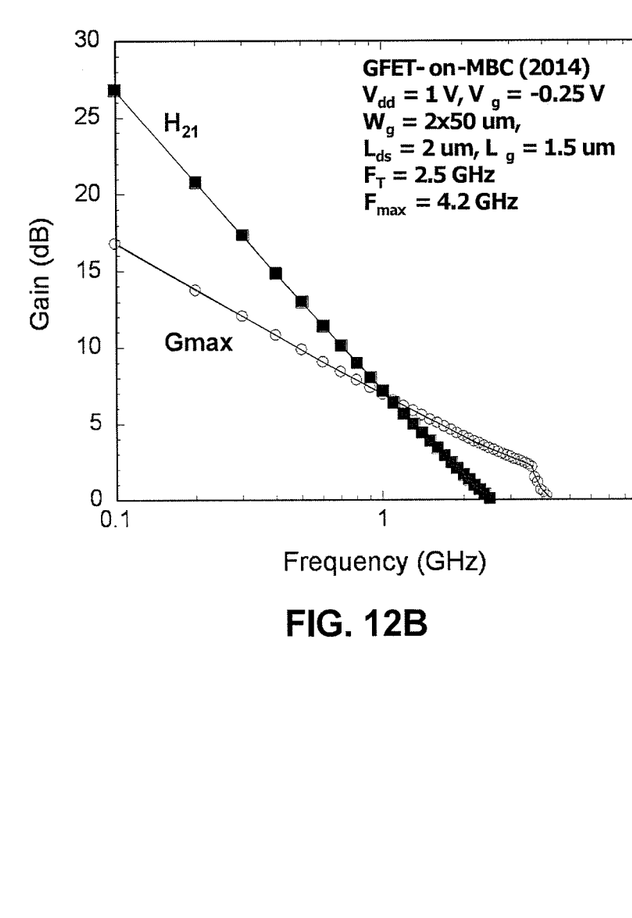

The radio frequency (RF) characteristics of a graphene FET on MBC are shown in FIGS. 12A and 12B. A maximum $F_T$ of 2.5 GHz and a maximum $F_{max}$ of 4.2 GHz have been measured for a graphene FET with $L_g$=1.5 μm, $L_{ds}$=2 μm, $W_g$=2×50 μm, which demonstrates that the graphene FET on MBC in accordance with the present disclosure operates in the GHz range.

The present disclosure has described graphene FETs fabricated on a biopolymer, such as microbial cellulose (MBC) and fabrication processes of graphene FETs on MBC and graphene sensors on MBC. These FETs and sensors may be used for in vivo electronics and sensor applications. Use of a biopolymer, such as MBC, provides a tissue/neuron-regenerative substrate for biosensors and bioelectronics, as demonstrated in FIGS. 8A and 8B. The used of CVD graphene and biopolymer substrates enables flexible and stretchable electronics and sensors for in vivo applications, such as a personal wireless body network.

Having now described the invention in accordance with the requirements of the patent statutes, those skilled in this art will understand how to make changes and modifications to the present invention to meet their specific requirements or conditions. Such changes and modifications may be made without departing from the scope and spirit of the invention as disclosed herein.

The foregoing Detailed Description of exemplary and preferred embodiments is presented for purposes of illustration and disclosure in accordance with the requirements of the law. It is not intended to be exhaustive nor to limit the invention to the precise form(s) described, but only to enable others skilled in the art to understand how the invention may be suited for a particular use or implementation. The possibility of modifications and variations will be apparent to practitioners skilled in the art. No limitation is intended by the description of exemplary embodiments which may have included tolerances, feature dimensions, specific operating conditions, engineering specifications, or the like, and which may vary between implementations or with changes to the state of the art, and no limitation should be implied therefrom. Applicant has made this disclosure with respect to the current state of the art, but also contemplates advancements and that adaptations in the future may take into consideration of those advancements, namely in accordance with the then current state of the art. It is intended that the scope of the invention be defined by the Claims as written and equivalents as applicable. Reference to a claim element in the singular is not intended to mean "one and only one" unless explicitly so stated. Moreover, no element, component, nor method or process step in this disclosure is intended to be dedicated to the public regardless of whether the element, component, or step is explicitly recited in the Claims. No claim element herein is to be construed under the provisions of 35 U.S.C. Sec. 112, sixth paragraph, unless the element is expressly recited using the phrase "means for . . . " and no method or process step herein is to be construed under those provisions unless the step, or steps, are expressly recited using the phrase "comprising the step(s) of . . . "

What is claimed is:

1. A method of making a device comprising:
    transferring a biopolymer membrane onto a handling wafer;
    forming a passivation layer on the biopolymer membrane;
    transferring graphene onto the passivation layer;
    patterning the graphene to form at least one graphene mesa;
    forming a source contact on the graphene mesa;
    forming a drain contact on the graphene mesa;
    etching the passivation layer surrounding the graphene mesa, the source contact, and the drain contact to expose the biopolymer membrane; and
    releasing the biopolymer membrane from the handling wafer.

2. The method of claim 1 further comprising:
    drying the biopolymer membrane after transferring the biopolymer membrane onto the handling wafer.

3. The method of claim 1 further comprising:
    forming a gate insulator on the graphene mesa; and
    forming a gate electrode on the gate insulator;
    wherein the gate electrode is between the source contact and the drain contact.

4. The method of claim 1 wherein the biopolymer membrane comprises microbial cellulose.

5. The method of claim 1 wherein the passivation layer comprises a dielectric.

6. The method of claim 1 wherein the passivation layer comprises:
    a dielectric on the biopolymer membrane; and
    a bio-compatible polymer on the dielectric.

7. The method of claim 6:
    wherein the dielectric comprises $Al_2O_3$, $SiO_2$, or $HfO_2$; and
    wherein the bio-compatible polymer comprises SU-8, polyimide, parylene, or polydimethylsiloxane (PDMS).

8. The method of claim 1 wherein the passivation layer comprises a bio-compatible polymer on the biopolymer membrane.

9. The method of claim 1 wherein the graphene comprises a chemical vapor deposition-grown graphene.

10. The method of claim 1 wherein the handling wafer comprises Si, Ge, InP, GaAs, $SiO_2$, sapphire, quartz, or glass.

11. The method of claim 1:
    wherein the biopolymer membrane has a thickness of less than 10 μm; and
    wherein the passivation layer comprises an atomic layer deposition of dielectric having a thickness of less than 10 nm, or wherein the passivation layer comprises a bio-compatible polymer having a thickness of about 1 μm.

12. The method of claim 1:
    wherein the biopolymer membrane is compatible with in vivo sensors and electronics.

* * * * *